(12) United States Patent
Perkins et al.

(10) Patent No.: US 6,753,188 B2
(45) Date of Patent: Jun. 22, 2004

(54) SURFACE PLASMON RESONANCE

(75) Inventors: Elaine Ann Perkins, Salisbury (GB);
David James Squirrell, Salisbury (GB)

(73) Assignee: The Secretary of State for Defence in Her Britannic Majesty's Government of the United Kingdom of Great Britain and Northern Ireland (GB)

(*) Notice: Subject to any disclaimer, the term of this patent is extended or adjusted under 35 U.S.C. 154(b) by 0 days.

(21) Appl. No.: 10/148,975

(22) PCT Filed: Dec. 7, 2000

(86) PCT No.: PCT/GB00/04665
§ 371 (c)(1),
(2), (4) Date: Jun. 3, 2002

(87) PCT Pub. No.: WO01/42768
PCT Pub. Date: Jun. 14, 2001

(65) Prior Publication Data
US 2002/0182743 A1 Dec. 5, 2002

(30) Foreign Application Priority Data
Dec. 7, 1999 (GB) .............................................. 9928849

(51) Int. Cl.[7] .............................................. G01N 21/64
(52) U.S. Cl. ................. 436/172; 422/82.05; 422/82.08; 356/445; 250/458.1; 250/459.1
(58) Field of Search .......................... 422/82.05, 82.08, 422/82.11; 436/172; 356/445; 250/458.1, 459.1

(56) References Cited
U.S. PATENT DOCUMENTS
3,975,084 A    8/1976   Block 5,341,215 A  * 8/1994  Seher .......................... 356/445

FOREIGN PATENT DOCUMENTS

| DE | 19650899    | 6/1998  |
|----|-------------|---------|
| EP | 0257955     | 3/1988  |
| EP | 0517930     | 12/1992 |
| GB | 2247749     | 3/1992  |
| GB | 2326229     | 12/1998 |
| WO | WO 96/02823 | 2/1996  |
| WO | WO 98/22808 | 5/1998  |

OTHER PUBLICATIONS

Barnes, W.L. and Sambles, J.E., "Re–Radiation From Surface–Plasmon–Polaritons by Surface Roughness," Solid State Communications, vol. 55, No. 11, pp. 921–923 (1985).

* cited by examiner

Primary Examiner—Jeffrey R. Snay
(74) Attorney, Agent, or Firm—Dean W. Russell; Kilpatrick Stockton LLP

(57) ABSTRACT

The surface plasmon resonance apparatus (1) for detecting a soluble and/or particulate analyte comprises a prism sensor (2) providing a metallised sensor surface (3) capable of binding the analyte, and a laser (10) providing a beam (4) for direction at the sensor surface (3). A detector (5) is provided which is capable of detecting light (6), which is internally reflected from the sensor surface (3). Displacement means (7) comprising a vibrator (8) and mirror (9), is operable whereby the excitation beam (4) is displaced over an angular range (A) relative to the sensor surface (3). An analyte sample (15) is disposed on the metallic sensor (3). The detector (5) is used to interpret the light signals (6) internally reflected from the sensor surface (3) so that the sample (15) is analysed. A video camera system (16), which includes a mirror (17), microscope objective (18) and CCD (charge-coupled device) array (19), is used to detect the scattered light emitted from the upper face of the sensor surface (3).

11 Claims, 7 Drawing Sheets

SURFACE PLASMON RESONANCE

This application claims priority to Great Britain Application No. 9928849.0 filed on Dec. 7, 1999 and International Application No. PCT/GB00/04665 filed on Dec. 7, 2000 and published in English as International Publication Number WO 01/42768 A1 on Jun. 14, 2001, the entire contents of each are hereby incorporated by reference.

TECHNICAL FIELD

The present invention relates broadly to surface plasmon resonance detection of analytes. The invention further relates to methods employing such apparatus.

BACKGROUND ART

The use of Surface Plasmon Resonance (SPR) for the detection of small soluble analytas from solution is well known (see e.g. "Advance in Biosensors—A Research Annual Vol 1. 1991" Ed. A P F Turner, Pub. Jai Press Ltd, London).

CB 2 271 886 (Secretary of State for Defence), to which reference should be made, discloses SPR apparatus comprising a light source for generating polarised light, a sensor, the outside of which is metal coated and may be contacted with a sample solution, and means for detecting the light which is internally reflected from the inner sensor surface.

In the absence of bound analyte, light is totally internally reflected at an incident angle characteristic of the refractive index (RI) of the sensor and of the sample solution. At a particular incident angel (the SPR angle), interaction of the metal with the evanescent wave set up by internal refection of the polarised light causes a drop in intensity of the reflected light. This drop can be observed using the light detector.

The binding of analyte to the sensor surface, within the evanescent wave zone, alters the RI of the area above the sensor and this perturbs the SPR angle. This perturbation can be observed using the light sensor and related to the surface concentration of analyte.

SPR detection in the literature has generally been limited to use with soluble molecular size analytes e.g. biomolecules such as proteins and nucleic acids which are specifically bound within the evanescent zone using appropriate liganda.

DISCLOSURE OF THE INVENTION

According to a first aspect of the present invention, surface plasmon resonance apparatus for detecting a soluble and/or a particular analyte is characterised in that it comprises:

(a) a sensor providing a metallised sensor surface capable of binding the analyte:

(b) a light source excitation beam for direction at the sensor surface:

(c) at least one detector capable of detecting light from the light beam which is internally reflected from the sensor surface, and (d) beam modifying means whereby the excitation beam is influenced in a controlled manner whereby the level of light emitted from the sensor surface is substantially enhanced.

The beam modifying means may be operable so as to displace the excitation beam over an angular range, relative to the sensor surface.

Alternatively, the beam modifying means may be operable so as to adjust the wavelength of the excitation beam.

According to a second aspect of the present invention, a method of detecting an analyte in a sample comprises exposing said sample to a metallised sensor surface and interpreting the light signals emitted from the sensor surface.

Possible analytes may include those particular or insoluble analytes containing or consisting of biomolecules, for instance bacteria or other cells, spores, virions etc., or biomolecules themselves such as proteins and polynucleotides.

Possible targets include cryptosporidium, E. coli, salmonella etc.

The excitation displacement means may comprise a beam-reflecting mirror and means for vibrating the mirror. The exitation beam may comprise a linear-beam, a fan-shaped beam or a wedge-shaped beam.

The excitation angle of displacement may be automatically adjustable according to changes detected in the SPR signal, thereby keeping the apparatus "on-resonance". Further adjustment may be required so as to take into account different areas of a matrixed sensor surface.

It will be advantageous to provide means for monitoring changes in resonance and light scattering emission so as to maintain a preferred angle of incidence.

Automatic scanning is preferred, whereby at any given position on the sensor surface the required condition for resonance and therefore substantially maximum scatter emission will be achieved.

Maximum surface emission conditions may be obtainable by use of appropriate controlled software, whereby, for example, each defined area of a matrixed surface during each single angle scan would take place in a time period less than 1.0 second.

A third aspect according to the invention comprises a microscope incorporating detection apparatus as hereinbefore described.

An embodiment of apparatus according to the invention will now be described by way of example only, with reference to the accompanying drawings wherein.

In the drawings, like reference numerals apply to like features and components.

Figure 1:
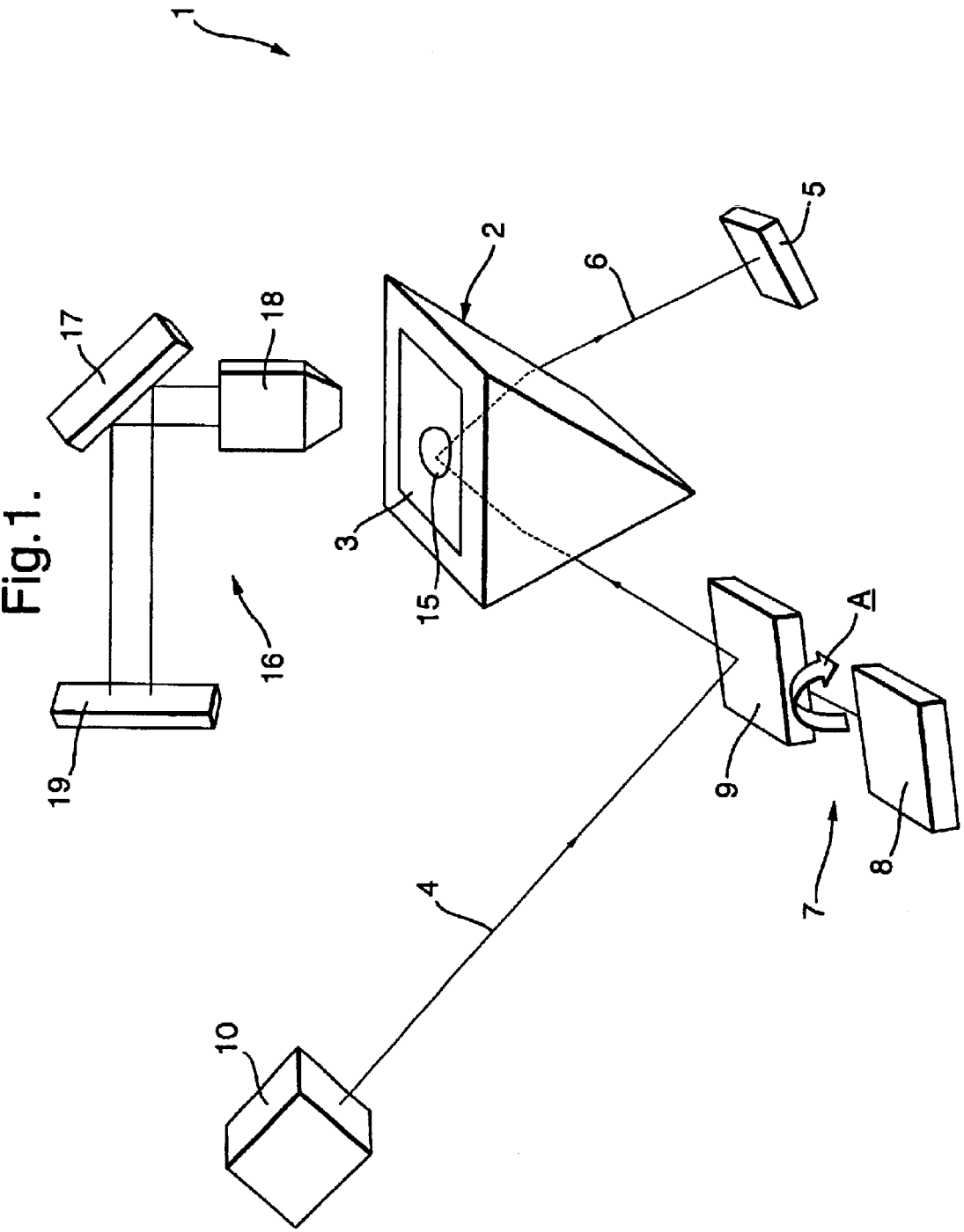
FIG. 1 is a diagrammatic illustration.

With reference to FIG. 1, surface plasmon resonance apparatus 1 for detecting a soluble and/or particulate analyte comprises a prism sensor 2 providing a metallised (gold layer) sensor surface 3 capable of binding the analyte, and, (in this example), a laser 10 providing a light source excitation beam 4 for direction at the sensor surface 3. A detector 5 is provided which is capable of detecting light 6 from the light beam 4, which light beam is internally reflected from the sensor surface 3, and displacement means 7 comprising a vibrator 8 and mirror 9, operable whereby the excitation beam 4 is displaced over an angular range A relative to the sensor surface 3.

The displacement means 7 operate to influence the excitation beam 4 in a controlled manner, whereby the level of light reflected from the sensor surface 3 and detected by the detector 5 is substantially enhanced and analytical sensitivity improved.

An analyte sample 15 is disposed on the metallic sensor surface 3 whereby it is exposed to said surface. The detector 5 is used to interpret the light signals 6 internally reflected from the sensor surface 3 so that the sample 15 is analysed.

A video camera system 16, which includes a mirror 17 and microscope objective 16 and CCD (charge-coupled device) array 19, is used to detect the scattered light emitted from the upper face of the sensor surface.

Figure 2:
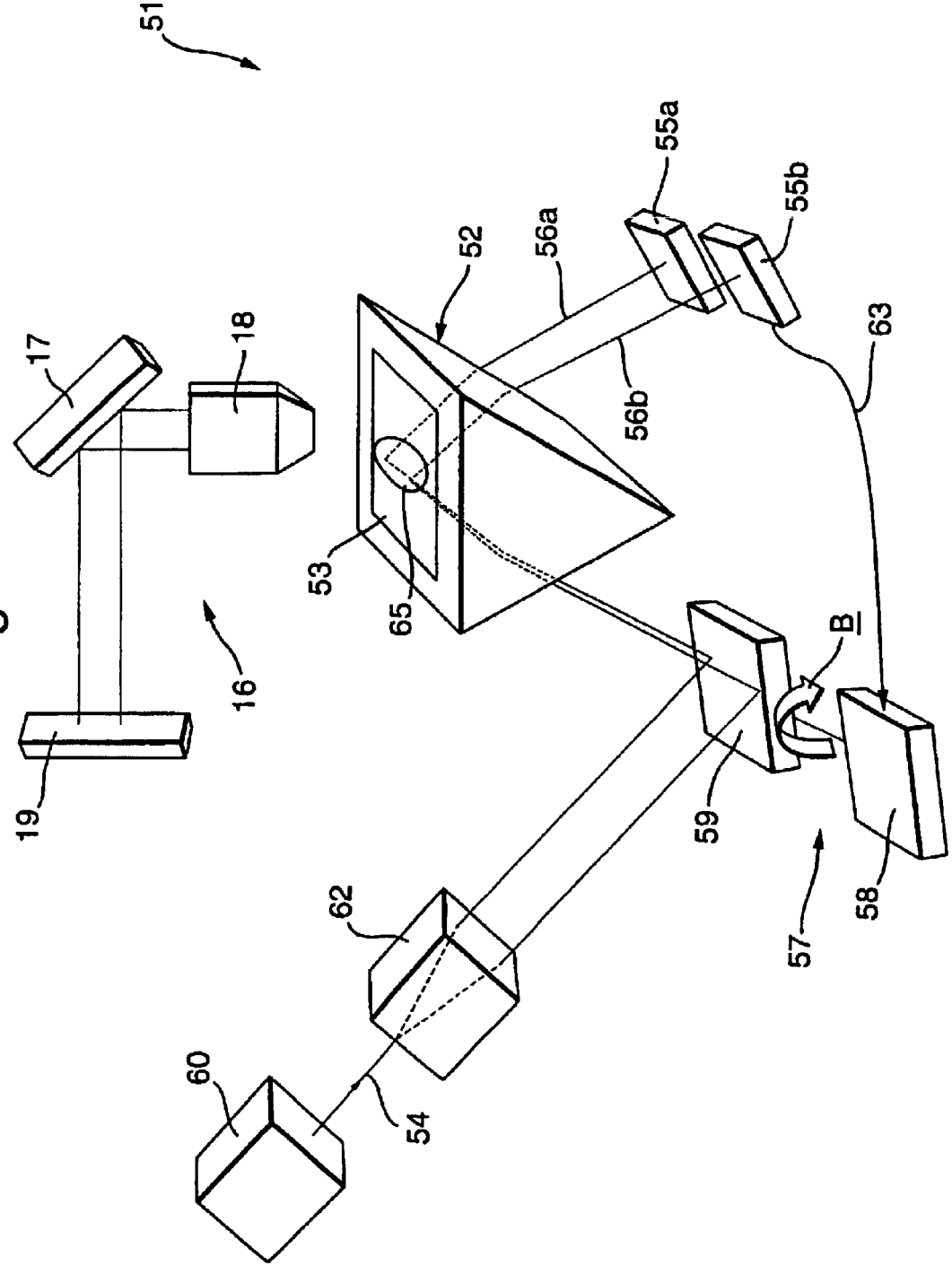
FIGS. 2 to 7 are further diagrammatic illustrations which illustrate modifications thereof.

FIG. 2 illustrates a modification wherein the surface plasmon apparatus 51 is provided with a feedback system.

The apparatus 51 is basically of the same form as apparatus 1 of FIG. 1. However, the apparatus 51 comprises a prism sensor 52 providing a gold layer sensor surface 53 and a laser 60 providing a light source excitation beam 54 for direction at the sensor surface 53. Two detectors 55a, 55b are provided which detect light 56a, 56b internally reflected by reflection form the sensor surface 53, and displacement means 57 comprising a vibrator 58 and mirror 59 operate to displace the excitation beam 54 (after it has been split into two components by a beam splitter 62, over an angular range B relative to the sensor surface 53.

In operation, the excitation beam 54 is split by the beam splitter 62 before impingement on the metallised surface 3 and then, after being internally reflected, on to twin detectors 55a, 55b. Detector 55a corresponds to detector 5 of FIG. 1, but detector 55b forms pan of a feedback loop 63 acting as a deepest SPR minimum detector which feeds back to the displacement or scanning means 57. This feedback optimises the system so as to ensure that the vibrating mirror 59 can be positioned at the deepest SPR minimum.

Thus, as in the case of the arrangement illustrated by FIG. 1, the level of light emitted from the sensor surface 53 and detected by the camera system 16, is substantially enhanced and analytical sensitivity improved, while detector 55a provides conventional SPR scan data.

Figure 3:
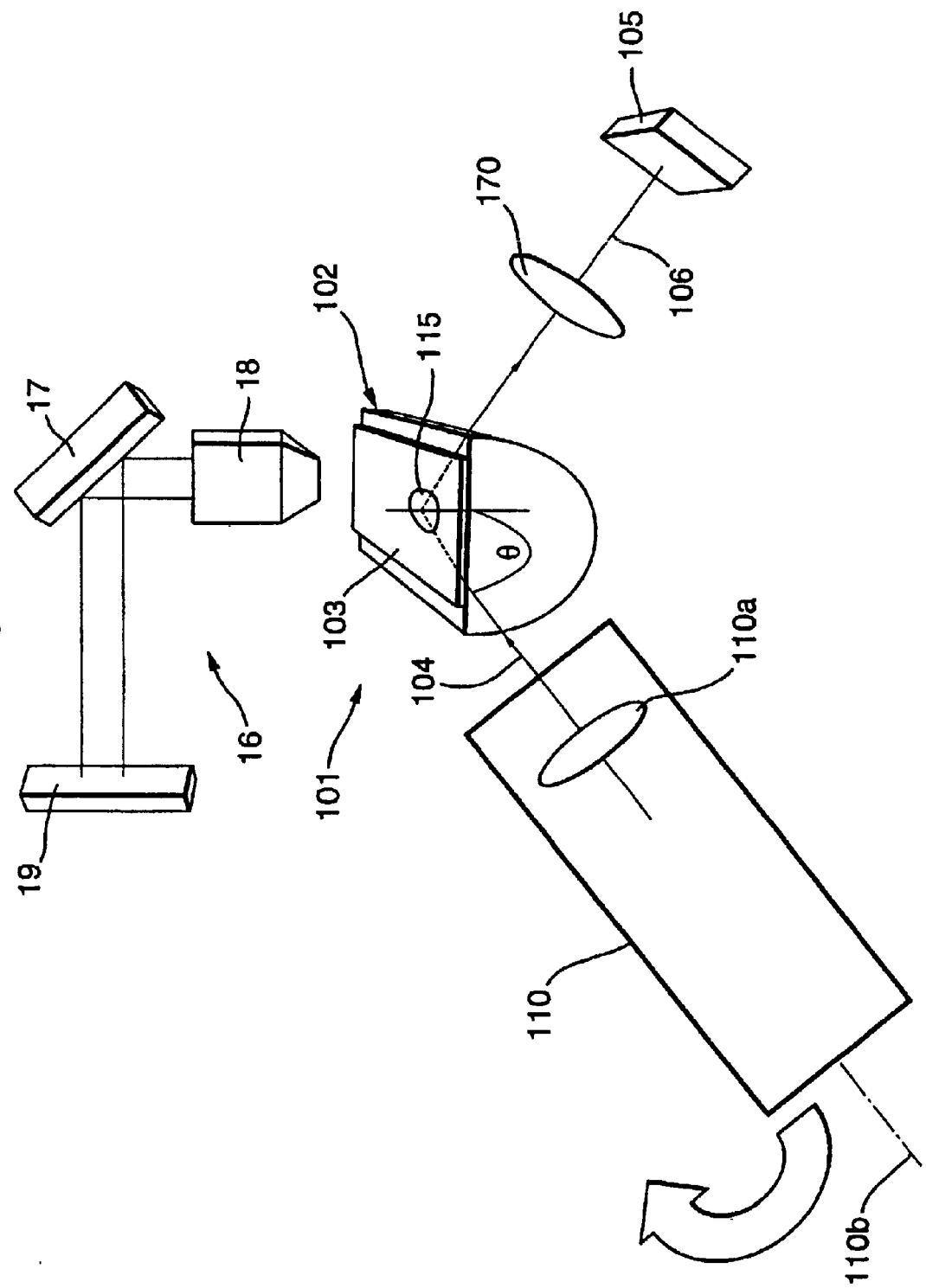

FIG. 3 illustrates a modified system 101 wherein a sensor block 102 of hemispherical shape is used to provide a metallised (gold) layer sensor surface 103.

A (laser) light source 110 with a focusing lens 110a provides an excitation beam 104 directed at the sensor surface 103.

Light 106 reflected from the sensor surface 103 passes through a lens 170 and is thereafter detected by sensor 105.

The laser 110 is operated, in a controlled manner, so that it is caused to rotate about axis 110h, which is coincident with beam 104, so that an angle θ is scanned by the beam.

Scattered light 106 emitted from the sensor layer 103 and detected by the detector 105 is measured at angle θ when maximum resonance occurs. SPR may be measured from the angle or time between light scattering maxima, or deepest SPR minima.

As before, the scattered light is substantially enhanced and analytical sensitivity improved by rotation of the excitation beam 104.

Figure 4:
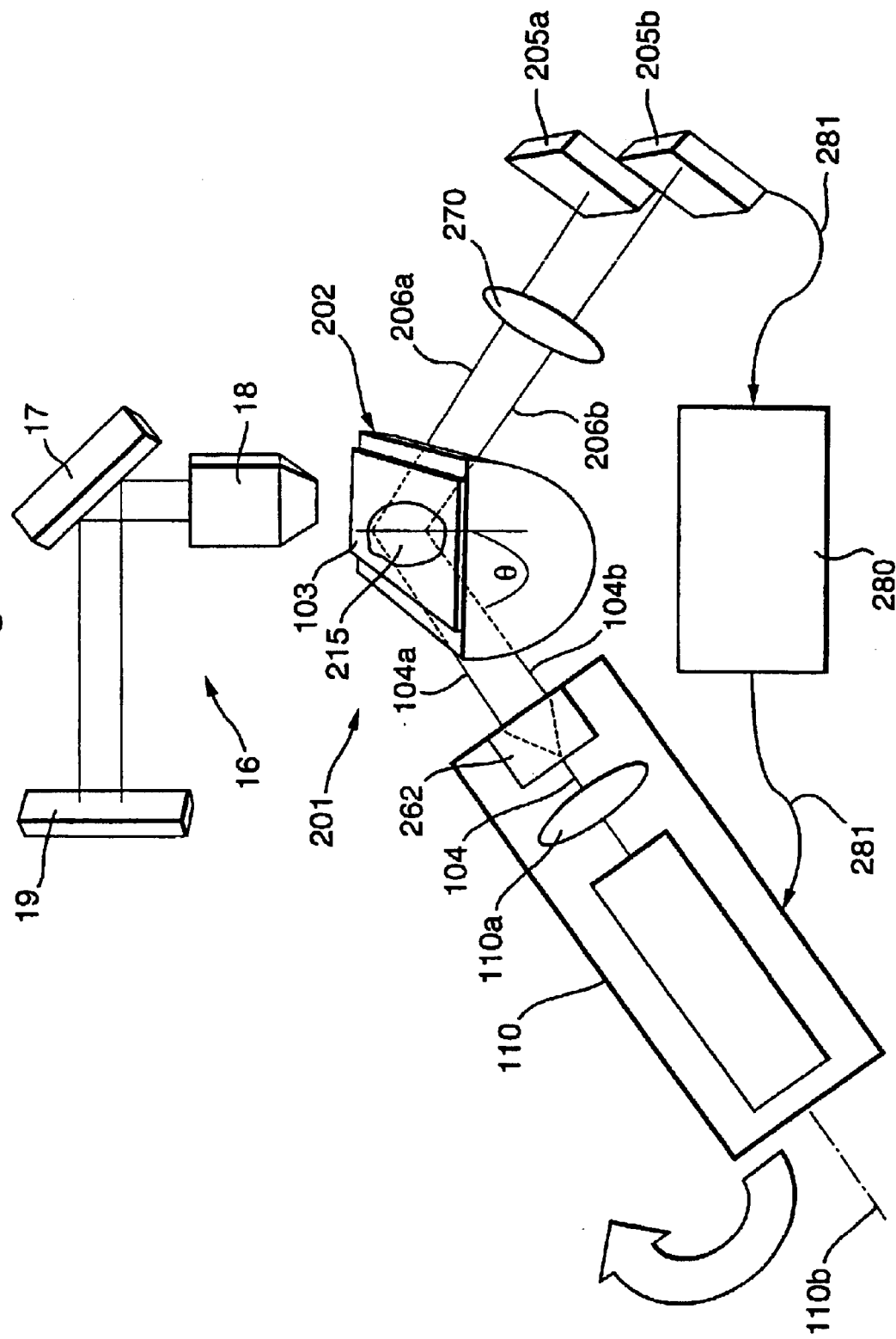

FIG. 4 illustrates a modification of the apparatus illustrated by FIG. 3, whereby feedback is provided in order to control the angular position of the beam 104.

The apparatus 201 illustration in FIG. 4 has a beam splitter 262, twin detectors 205a and 205b, a stepper motor controller 280 for rotating the laser 110, and a feedback loop 281.

A beam splitter 262 is provided, so as to divide the twin beams 104a, 104b.

The apparatus 201 allows angle θ to be set for maximum resonance and then adjusted incrementally to maintain resonance maximum using readout from the SPR detector 209b.

Figure 5:
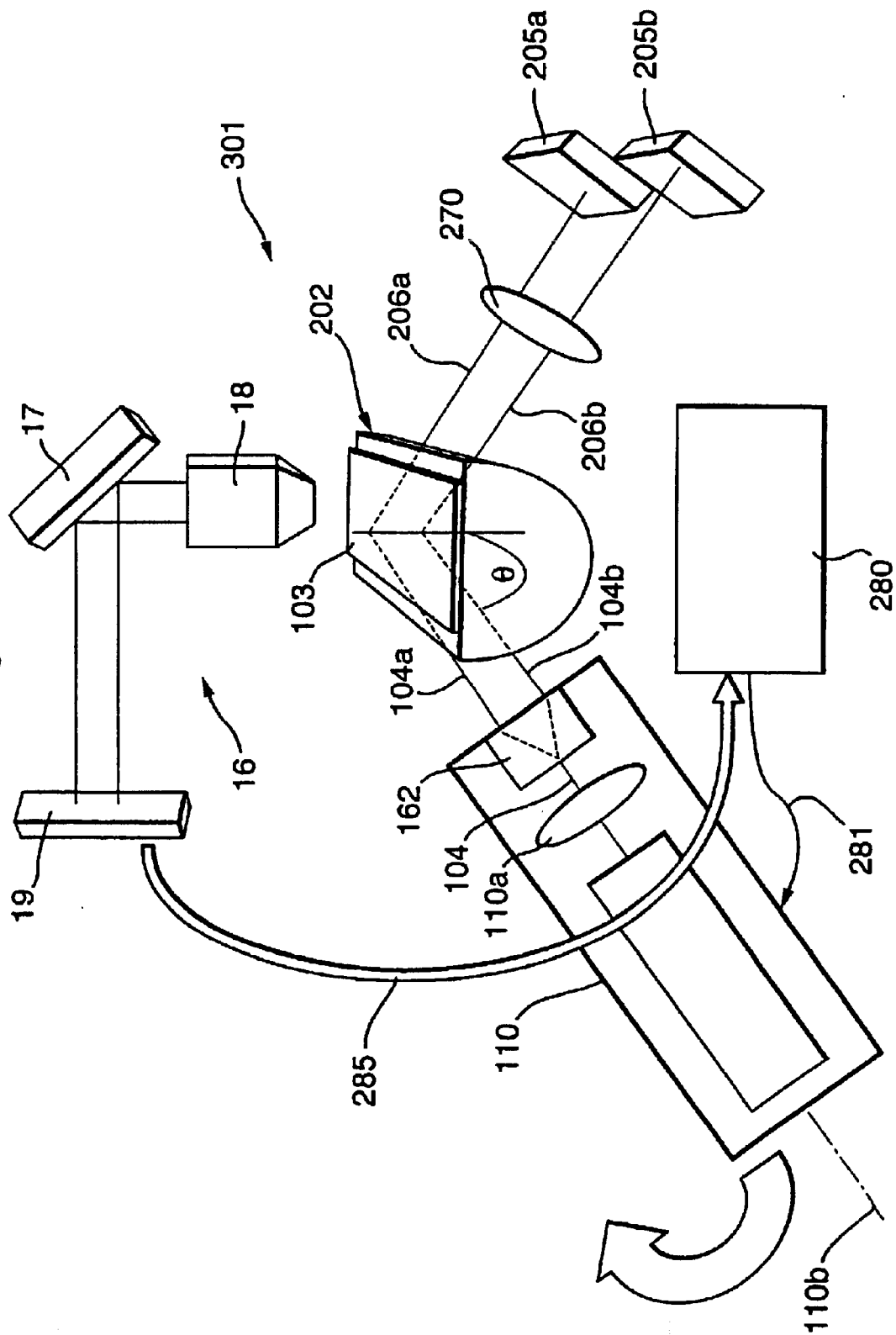

FIG. 5 illustrates apparatus 301 wherein, instead or using the SPR signal and using it to adjust the angle θ as in FIG. 4, the light scattering signal is used to set the angle for maximum resonance.

The video camera system 16 is used to send a feedback signal to the stepper motor control 280, along signal line 285 when maximum light is achieved which in turn sends a feedback signal to the laser 110, along signal line 281.

FIG. 5 also illustrates how SPR can be monitored from light scattering by determining the change in angular position θ.

Figure 6:
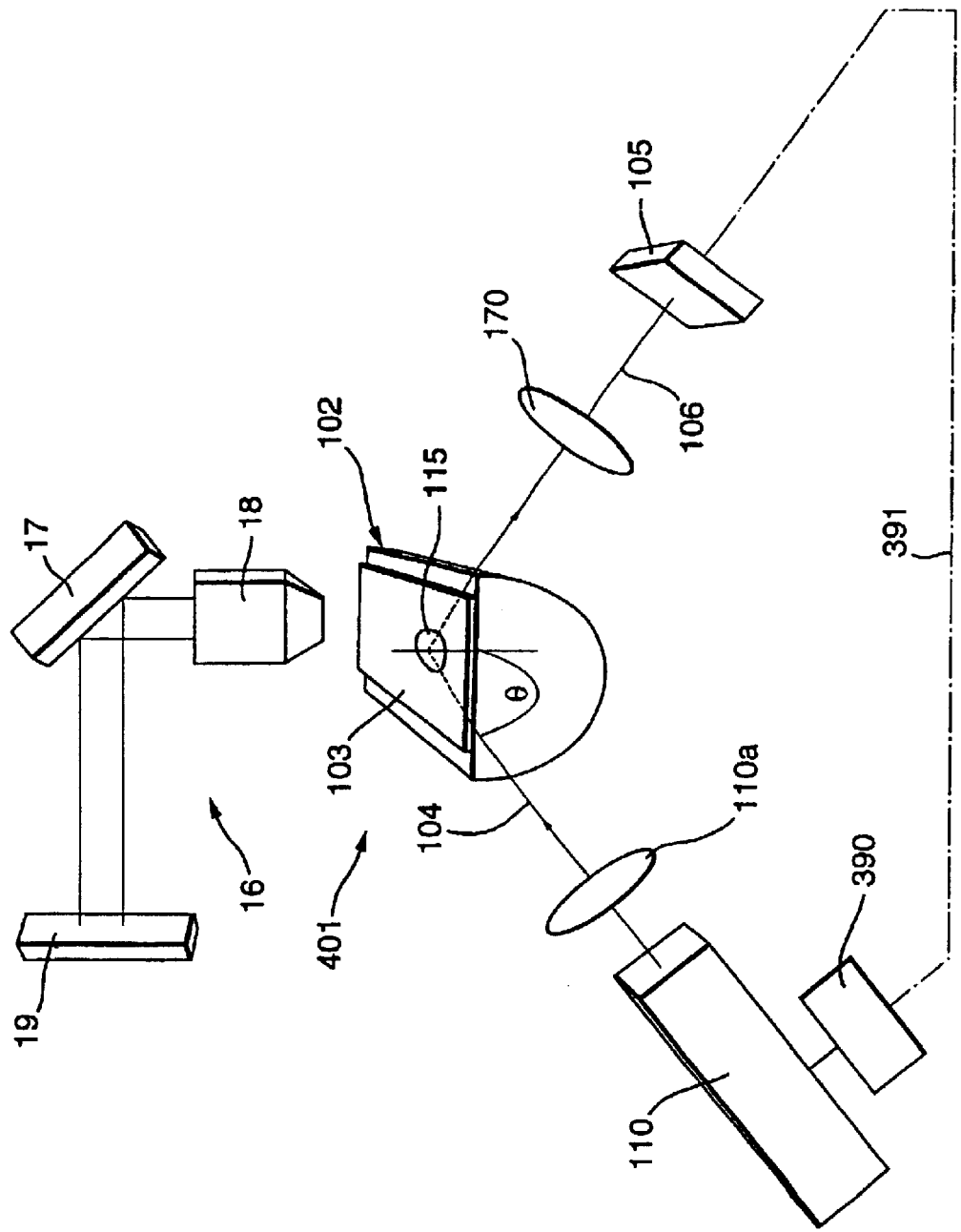

FIG. 6 illustrates apparatus 401. Here angle θ is maintained, and the wavelength of excitation beam 104 automatically scanned and adjusted, using beam modifying means comprising control unit 390.

SPR can here be measured using the adjustable wavelength of the excitation beam 104. A feedback line 391 may be provided between the detector 105 and the control unit 390, whereby the detector is used to scan and adjust the excitation beam 104 according to feedback signals emitted along line 391.

Figure 7:
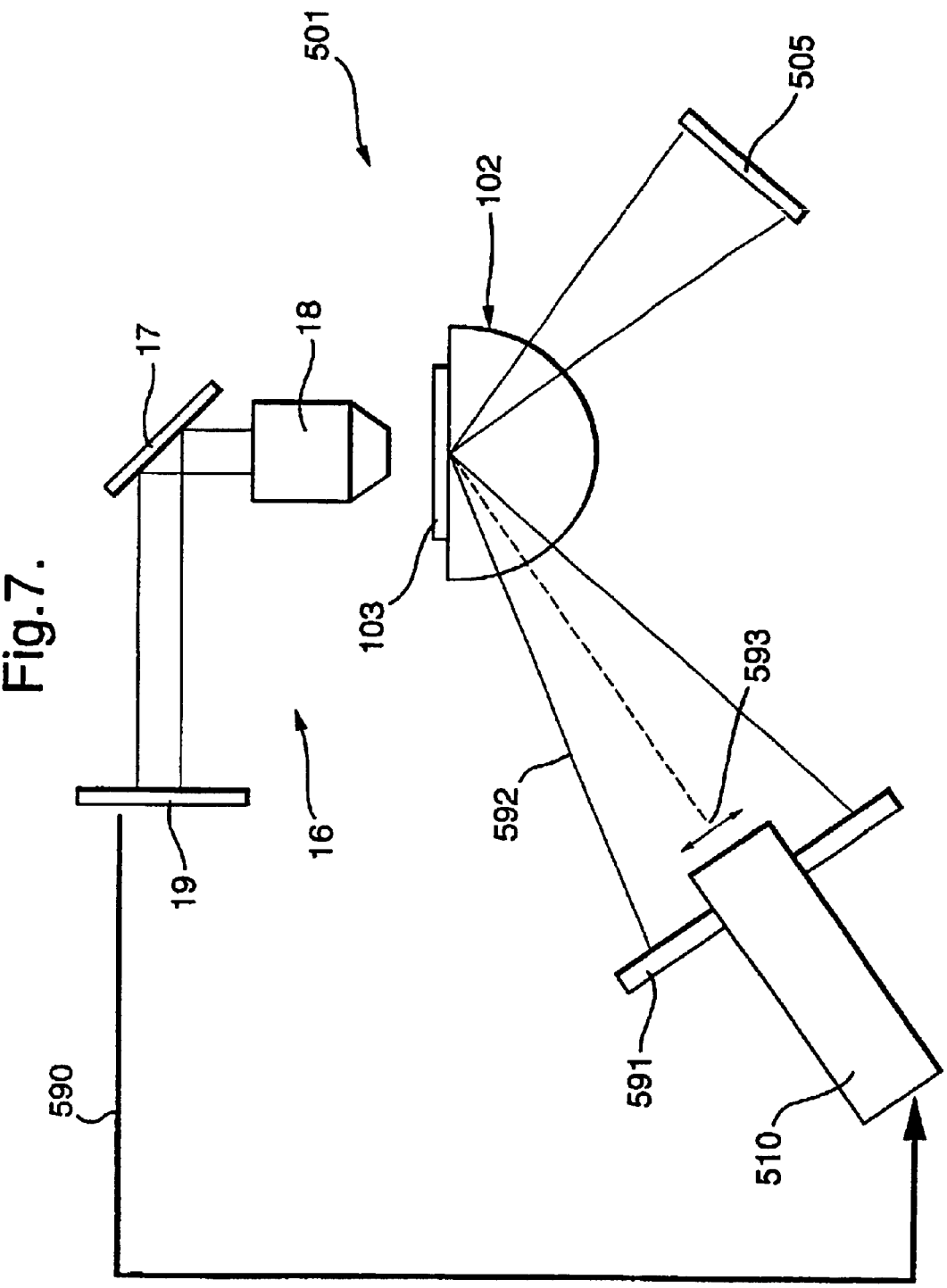

FIG. 7 illustrates apparatus 501 which is a variant of the arrangement shown by FIG. 5, but which provides enhanced resolution by improving angular resolution and control.

FIG. 7 shows use of a (laser) light source 510 which receives a feedback control signal 590 from the video camera system 16, whereby a large fixed angle excitation beam 592 of wedge form is provided by a second light force 591, as well as a small angle beam 593. The beam 593 is adjustable, so that it may be "tuned" for optimised light scatter.

The present invention may also reside in a microscope incorporating detection apparatus as hereinbefore described.

The invention may be used with analytes including a particulate or insoluble analyte containing or consisting of bimolecular, spores, or virions. Alternatives may comprise bacteria or optical markers such as gold gel, latex beads or florescent markers.

Any of the features disclosed herein may, where practicable, be added to or substituted for any of the other features disclosed herein.

What is claimed is:

1. A surface plasmon resonance apparatus for detecting soluble and/or particulate analytes, comprising a sensor having a lower surface and an upper metallised sensor surface providing means for binding the analytes thereto, a light source providing an excitation beam contacting the lower surface of the sensor, a first detector, positioned above the upper surface of the sensor, for detecting light scattered from a bound analyte, a second detector, positioned below the lower surface of the sensor, for detecting light reflected therefrom and means for enhancing the scattered light by modification of the excitation beam through feedback control means from the first detector.

2. The apparatus according to claim 1, wherein the feedback control means comprises automatic adjustment means adjusting the wavelength of the excitation beam.

3. The apparatus according to claim 2, in which the excitation beam comprises a first linear beam and a second wedge shaped beam.

4. The apparatus according to claim 2, wherein the first detector comprises a charge-couple device.

5. The apparatus according to claim 1, wherein the feedback control means comprises automatic adjustment means displacing the excitation beam over a range of angles with respect to the lower surface of the sensor.

6. The apparatus according to claim 5, in which the excitation beam comprises a first linear beam and a second wedge-shaped beam.

7. The apparatus according to claim 5 wherein the first detector comprises a charge-couple device.

8. A method of detecting soluble and/or particulate analytes based on surface plasmon resonance, comprising the steps of i) directing an excitation beam at the lower surface of a sensor comprising an upper metallised sensor surface including means for binding an analyte thereto, ii) detecting light scattered by bound particulate, iii) detecting light reflected from the lower surface at a second detector, and iv) enhancing the light scattered by modification of the excitation beam through feedback control means from the first detector.

9. The method according to claim 8, wherein the feedback control means automatically adjusts the wavelength of the excitation beam.

10. The method according to claim 8, wherein the feedback control means automatically adjusts the angle of incidence of the excitation beam with respect to the sensor surface.

11. The method according to claim 8, wherein the particulate or insoluble analytes comprise an analyte selected from the group consisting of bacteria, spores, and virions.

* * * * *